United States Patent [19]

Copp et al.

[11] Patent Number: 5,049,637

[45] Date of Patent: Sep. 17, 1991

[54] 1,2,3,4,10,14B-HEXAHYDRODIBENZO[C,F] PYRAZINO-[1,2-A]AZEPINO DERIVATIVES AND 10-AZA, 10-OXA AND 10-THIA ANALOGUES

[75] Inventors: Frederick C. Copp, Beckenham, England; Alan L.A. Boura, Beaconfield; William R. Jackson, Glen Waverley; John D. Cullen; Endeavour Hills, all of Australia

[73] Assignees: Monash University, Clayton; Australasian Drug Development Limited, South Melbourne, both of Australia; a part interest

[21] Appl. No.: 427,840

[22] PCT Filed: Mar. 31, 1988

[86] PCT No.: PCT/AU88/00095

§ 371 Date: Dec. 7, 1989

§ 102(e) Date: Dec. 7, 1989

[87] PCT Pub. No.: WO88/07997

PCT Pub. Date: Oct. 20, 1988

[30] Foreign Application Priority Data

Apr. 10, 1987 [AU] Australia .................................. PI1363

[51] Int. Cl.$^5$ ............................................ C07D 487/04
[52] U.S. Cl. ................................... 528/44; 540/546; 540/578; 540/579

[58] Field of Search ................ 540/546, 578, 579; 528/44

[56] References Cited

U.S. PATENT DOCUMENTS 3,534,041 10/1970 Van Der Burg et al. ........... 260/268

FOREIGN PATENT DOCUMENTS 415312 6/1971 Australia .
423307 4/1972 Australia .
0126343 11/1984 European Pat. Off. .

*Primary Examiner*—Maurice J. Welsh
*Attorney, Agent, or Firm*—Finnegan, Henderson, Farabow, Garrett & Dunner

[57] ABSTRACT

A compound of general formula (I), wherein $X=CH_2$, O, S or $NR^4$, and Y=formula (II): where $R^1=H$, lower alkyl or an aryloxyalkyl group, wherein the aryl group is optionally substituted by alkyl, alkoxy, hydrogen, alkyl substituted by hydrogen, and n is an integer between 0 and 5, and $Z=O$, S or $NR^2$; wherein $R^2=H$, lower alkyl, hydroxy, amino cyano or acyl, $R^3=H$, or lower alkyl, and $R^4=H$, lower alkyl, or lower acyl, and pharmaceutically acceptable salts thereof.

30 Claims, No Drawings

1,2,3,4,10,14B-HEXAHYDRODIBENZO[C,F-]PYRAZINO-[1,2-A]AZEPINO DERIVATIVES AND 10-AZA, 10-OXA AND 10-THIA ANALOGUES

This invention relates to novel structural analogues and derivatives of the compound normianserin, and to methods of synthesis and therapeutic uses thereof.

BACKGROUND AND PRIOR ART

Mianserin (1,2,3,4,10,14b-hexahydro-2-methyl-dibenzo [c,f]pyrazino[1,2-a]azepine) is a serotonin inhibitor and antihistamine compound whose preparation was disclosed in U.S. Pat. No. 3,534,041 to Organon. Derivatives of this compound are disclosed in British Patents No. 1498632 and 1498633.

Normianserin (Chemical Abstracts no. 71936-92-0), also known as desmethylmianserin, has similar pharmacological activity to that of mianserin but is less potent (Pinder, R. M. (1985) Acta Psychiatrica Scand. Act. 320 1-9; Doggrell, S. (1985) J. Pharm. Pharmacol. 37 116-20; Przegalinski, E., Rawlow, A., and Dohnal-Borak, 1. (1986) Polish J. Pharmacol. Pharm. 38 69-75).

A related class of dibenzo-pyrazino-azepines was disclosed in U.S. Pat. No. 3,701,778 (van der Burg). These compounds were stated to have anti-inflammatory, anti-serotonergic, anti-histamine and cardiovascular effects, while certain intermediates in their preparation were also pharmacologically active. The compounds included oxazepines, thiazepines and diazepines, and a variety of synthetic routes for obtaining the desired products was set forth.

It is known that many important pharmacological effects are mediated by 5-hydroxytryptamine, which is also known as serotonin. More recently, it has been established that receptors for 5-hydroxytryptamine are of five distinct sub-types, each having a characteristic pharmacological profile (reviewed by Fozard, J. R. (1987) Trends in Pharmacological Sciences 8 501-506). A variety of physical and mental conditions, such as migraine, depression, anxiety, and gastrointestinal disturbances, is susceptible to manipulation using agonists and antagonists of 5-hydroxytryptamine with binding activity at the different types of receptors. Mianserin, ketanserin, ritanserin and altanserin are all cited by Fozard (op. cit.) as being 5-$HT_2$-receptor antagonists.

SUMMARY OF THE INVENTION

The present invention provides compounds of the general formula I

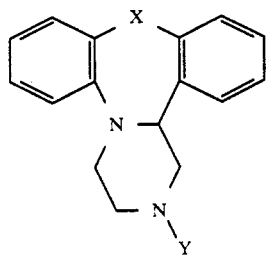

wherein
$X = CH_2$, O, S or $NR^4$,

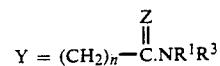

where $R^1$ = H, lower alkyl or aryloxyalkyl group wherein the aryl group is optionally substituted by alkyl, alkoxy, halogen, alkyl substituted by halogen, and n is an integer between 0 and 5, and $Z = O$, S or $NR^2$ wherein $R^2$ = H, lower alkyl, hydroxy, amino, cyano, or acyl, $R^3$ = H or lower alkyl, and $R^4$ = H, lower alkyl, or lower acyl.

Where appropriate, the invention also includes pharmaceutically acceptable salts of these compounds. Both D-and L-isomers are within the scope of the invention.

According to another aspect of the invention, methods for preparation of the compounds of formula I are provided, as set out hereinbelow:

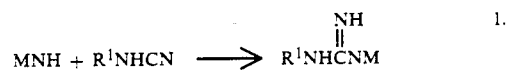

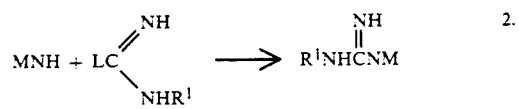

where MNH=normianserin and L is a suitable leaving group, for example $CH_3O$, $CH_3S$, $CH_3SO_2$, $SO_3H$,

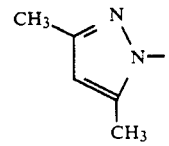

(3,5-dimethylpyrazol-1-yl), etc.

Compounds according to formula I wherein Z=S not only possess useful therapeutic activity per se, but may also be used as intermediates for preparation of compounds of formula I wherein $Z=NR^2$:

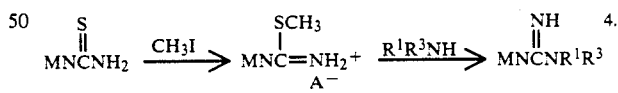

where A is a halogen.

An alternative method of synthesis of compounds of formula I is illustrated by the equation:

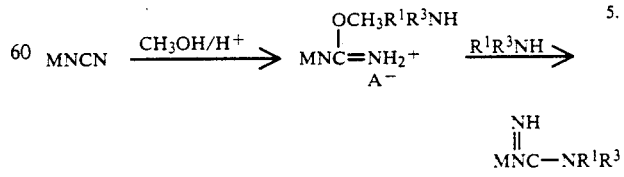

Compounds according to formula I wherein $Z=NH_2$ may also be prepared for example from N-cyanonormianserin (i.e. formula I wherein $X=CH_2$, and Y=CN) and the appropriate metallated residue (for example sodamide or metallated amines):

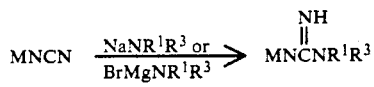

6.

Essentially all of the compounds are derived from normianserin, which may itself be obtained from mianserin by a variety of routes.

The compounds, where $X=CH_2$, may be prepared by the nucleophilic attack of normianserin on the appropriate reagents, including S,S-dimethyl N-cyanodithioiminocarbonate (i.e.: $(MeS)_2C:NCN$), 2-chloroacetamide, cyanamide, acrylamide, and 3-bromopropyl-1-cyanide, to yield appropriate compounds which can undergo further reactions, such as the conversion of a nitrile into amidocarbonyl, replacement of methylthio by ethylamino, etc. Further reactions also include the conversion of N-cyanonormianserin with sodamide to give the parent 2-carboxamidinonormianserin; or by conversion of the N-cyanonormianserin into the corresponding 2-[S-methylisothiocarboxamido]normianserin, which can then be reacted further with the appropriate amines to give derivatives of 2-carboxamidinonormianserin, etc.

Other methods for preparation of compounds according to formula I will be apparent to those of normal skill in the art, and are specifically included within the scope of the present invention.

In particular, it will be apparent that methods suitable for synthesis of compounds of formula I in which X is O, S or $NR^4$ are known, for example with reference to the aforementioned U.S. Pat. No. 3,701,778.

These reactions are performed on racemic mixtures; however, it will be apparent to those skilled in the art that these procedures are equally applicable to D- or L-isomers.

According to a third aspect of the invention there is provided a method of treatment of disturbances of 5-hydroxytryptamine metabolism in a mammal, comprising the step of administering to a mammal suffering from such disturbance a pharmacologically effective amount of a compound according to formula I.

According to a fourth aspect of the invention, there are provided compositions containing as an effective agent compounds according to formula I, together with pharmaceutically acceptable carriers, diluents, or excipients.

DETAILED DESCRIPTION OF THE INVENTION

Preparation of compounds according to the invention is illustrated by reference to the following non-limiting examples. All temperatures are given in degrees Celsius. It will be appreciated by persons skilled in the art that other synthetic routes may be suitable for preparation of the desired compounds.

EXAMPLE 1 (FCC 4)

2-Cyano-1,2,3,4,10,14b-hexahydrodibenzo[c,f]pyrazino[1,2-a]azepine. 2-Cyanonormianserin A solution of mianserin (5.2 g) in anhydrous benzene (20 ml) was added slowly to a stirred solution of cyanogen bromide (2.3 g) in anhydrous benzene (20 ml) in an atmosphere of nitrogen. After 24 hours, the mixture was diluted with diethyl ether (50 ml) and shaken with water (50 ml). The separated aqueous layer was back extracted with a mixture of benzene and ether (equal volumes of each, total 50 ml) and the combined organic layers dried over anhydrous potassium carbonate and then evaporated under reduced pressure. The residual solid was recrystallised from ethanol to give 2-cyanonormianserin as colourless needles m.p. 164°–166° C. This compound is outside general formula I, and was used as an intermediate only.

EXAMPLE 2 (FCC 5)

2-Carboxamidino-1,2,3,4,10,14b-hexahydrodibenzo[c,f]pyrazino[1,2-a]azepine Hydrochloride A solution of sodamide in liquid ammonia was prepared in the usual way from metallic sodium (0.35 g) in dried liquid ammonia (150 ml) in the presence of a trace of ferric nitrate. The reaction mixture was kept at about −70° and moisture was rigorously excluded. 2-Cyanonormianserin (3.4 g) was then added slowly and the mixture stirred whilst dried hexamethylphosphoric triamide (HMPA) was added dropwise until the 2-cyanonormianserin began to dissolve; about 1 ml of HMPA was required. A deep brown solution was formed. The stirring was continued for 30 minutes and the solution poured cautiously into a solution of ammonium chloride (4 g) in iced water (150 ml). The resulting suspension was kept for some 30 minutes at room temperature and the solid then filtered off and washed with a little water. The residue (a) was reserved. The combined filtrate and washings were concentrated in vacuo to about 25 ml, when a second crop of solid (b) separated. The two crops (a) and (b) were combined and recrystallised from isopropanol to give 2-carboxamidino-1,2,3,4,10,14b-hexahydro[c,f]-pyrazino[1,2-a]azepine hydrochloride as a colourless solid; it melted at 290°–300° C. with decomposition. The product had variable water content, depending on the drying procedure used.

EXAMPLE 3 (FCC 11T)

2-(2-Imidazolino)-1,2,3,4,10,14b-hexahydrodibenzo[c,f]pyrazino[1,2-a]azepine p-toluenesulphonate A mixture of 2-cyanonormianserin (1.0 g) and 2-aminoethylammonium p-toluenesulphonate (2.0 g) in propan-1-ol (10 ml) was heated to reflux for 24 hours in an atmosphere of nitrogen. The reaction solution was then poured into water (50 ml) and the resulting mixture extracted with methylene dichloride (3×25 ml). The combined extracts were washed with water (3×25 ml), dried over magnesium sulphate and evaporated to give a colourless oil. Fractional crystallization of this oil from propan-2-ol gave the required 2-(2-imidazolino)-1,2,3,4,10,14b-hexahydrodibenzo [c,f]pyrazino[1,2-a]azepine p-toluenesulphonate. It was a colourless crystalline solid, m.p. 220°–221° C.

It will be apparent tht this compound may then be oxidized to produce the corresponding imidazolyl compound.

EXAMPLE 4 (FCC 9)

2-Thiocarboxamido-1,2,3,4,10,14b-hexahydrodibenzo[c,f]pyrazino[1,2-a]azepine

Dry hydrogen sulphide was passed through a solution of 2-cyanonormianserin (500 mg) in a mixture of triethylamine (0.25 ml) and pyridine (25 ml) for 24 hours. The resulting solution was poured into water (150 ml) and the mixture stirred for 30 minutes at room temperature to afford colourless crystals which were filtered off, washed with fresh water and dried in vacuo. Recrystallization from a mixture of diethyl ether and light petroleum gave colourless needles of the desired compound, m.p. 214°–216° C.

EXAMPLE 5 (FCC 13)

2-Carboxamido-1,2,3,4,10,14b-hexahydrodibenzo[c,f]pyrazino[1,2-a]azepine

A slurry of 2-cyanonormianserin (0.55 g) in aqueous hydrogen peroxide (100 Vol, 0.51 ml) and 20% aqueous sodium hydroxide (0.51 ml) was stirred for 30 minutes, during which time the reaction mixture became warm, then cooled to room temperature, and some oxygen was evolved. Three portions of methanol (3×2 ml) were added to the reaction mixture, at 30 minute intervals with stirring. The mixture was warmed to 60° for 15 minutes, then poured into water (50 ml) to give a white precipitate which was filtered at the pump, washed with water (2×10 ml) and dried in vacuo to give 2-carboxamido-1,2,3,4,10,14b-hexahydrodibenzo[c,f]pyrazino[1,2-a]azepine as a colourless solid, m.p. 186°–187°.

EXAMPLE 6 (FCC 2)

1,2,3,4,10,14b-Hexahydrodibenzo[c,f]pyrazino[1,2-a]azepine. Normianserin

A mixture of 2-cyanonormianserin (see Example 1) (3.75 g), conc. hydrochloric acid (20 ml) and water (20 ml) was heated to reflux with stirring. After 12 hours the mixture was cooled, when a solid separated from solution. This was filtered off and dried in vacuo (3.65 g) m.p. 134°–135°. It was then treated with conc. ammonia (20 ml) in water (100 ml) and the mixture extracted three times with methylene dichloride (50 ml each time). The combined extracts were dried over potassium carbonate, filtered and evaporated to give normianserin which was recrystallised from a mixture of propan-2-ol and water as a crystalline solid, m.p. 83°–84°.

The compound is outside general formula I, and was used as an intermediate only.

EXAMPLE 7 (FCC 14)

2-(N-Cyano-N'-ethyl-carboxamidino)-1,2,3,4,10,14b-hexahydrodibenzo[c,f]pyrazino[1,2-a]azepine A mixture of normianserin (500 mg) and S,S'-dimethyl N-cyanodithioiminocarbonate (292 mg) and ethanol (50 ml) was stirred at room temperature for 48 hours; methane thiol was evolved and a precipitate was formed. The solvent was removed under reduced pressure and the residue triturated with cold water (50 ml). The residual solid was collected and recrystallised from a mixture of propan-2-ol and ether. A solution of ethylamine (3 ml) in ethanol (20 ml) was added to a stirred suspension of the solid in ethanol (20 ml); after 12 hours there was a further addition of ethylamine (1 ml) in ethanol (20 ml) and the stirring was then continued for a further 12 hours. The solvent was then evaporated and the resulting gum chromatographed (silica; 40% ethyl acetate in light petroleum to 100% ethyl acetate). The resulting oil was dissolved in hot propan-2-ol (5 ml) and the resulting solution diluted with light petroleum (150 ml). A pale yellow solid was formed, collected and dried in vacuo to give 2(N-cyano-N'-ethylcarboxamidino)-1,2,3,410,14b-hexahydrodibenzo[c,f]pyrazino[1,2-a]azepine, m.p. 205°–206°.

EXAMPLE 8 (FCC 10)

2-[S-Methyl-isothiocarboxamido]-1,2,3,4,10,14b-hexahydrodibenzo[c,f]pyrazino[1,2-a]azepine hydriodide Methyl iodide (0.15 ml) was added to a suspension of 2-thiocarboxamido-1,2,3,4,10,14b-hexahydrodibenzo[c,f]pyrazino[1,2-a]azepine from Example 4 (0.5 g) in methanol (25 ml) and the mixture heated to reflux for 3 hours. The solvent was removed and the residual gum stirred with ethyl acetate (3×10 ml). The resulting solid product was collected and dried in vacuo, m.p. 209°–211° (decomp).

This compound is outside general formula I and was used as an intermediate only.

EXAMPLE 9 (FCC 12)

2-(N-2-Phenoxyethyl carboxamidino)-1,2,3,4,10,14b-hexahydrodibenzo[c,f]pyrazino[1,2-a]azepine hydrochloride A mixture of the S-methylisothiocarboxamido hydroiodide (S-methylisothiouronium iodide) from Example 8 (680 mg) and 2-phenoxyethylamine (2.5 g) in propan-1-ol (25 ml) was heated to reflux for 24 hours. Dilution of the cooled reaction mixture with ether afforded a cream coloured solid. This was collected, dissolved in ethanol (10 ml) and the solution passed through Amberlite IRA 400 (Cl⁻) ion exchange resin. Evaporation of the eluate gave the desired hydrochloride as a pale yellow microcrystalline solid, m.p. 250°–253°. Amberlite is a trade mark of Mallinckrodt Australia Pty. Ltd.

EXAMPLE 10 (FCC 15)

2-(N-Ethylcarboxamido)-1,2,3,4,10,14b-hexahydrodibenzo[c,f]pyrazino[1,2-a]azepine A solution of normianserin (1.5 g) in dry benzene (20 ml) was added to a stirred solution of ethyl isocyanate (0.43 g) in dry benzene (20 ml) and the mixture stirred for 48 hours. The solvent was then evaporated and the residue crystallised from propan-2-ol to give the desired 2-(N-ethylcarboxamido)-1,2,3,4,10,14b-hexahydrodibenzo[c,f]pyrazino[1,2-a] azepine as a cream coloured solid m.p. 206°–207°.

EXAMPLE 11 (FCC 17)

2-(N-Ethylcarboxamidino)-1,2,3,4,10,14b-hexahydrodibenzo[c,f]pyrazino[1,2-a]azepine hydrochloride A solution of the 2-[S-methylisothiocarboxamido] hydriodide derivative from Example 8 (0.5 g) and ethylamine (0.1 ml) in propan-1-ol (25 ml) was heated to reflux for 12 hours in an atmosphere of nitrogen. The solvent was removed and the residue was dissolved in ethanol (5 ml) and the resulting solution percolated through Amberlite IRA-400 (Cl⁻) ion exchange resin. The eluate was evaporated and the residue purified by preparative high performance liquid chromatography on a Deltapak C18 column (30 cm×19 mm) in a normal gradient of 20% aqueous methanol −0.1% trifluoroacetic acid to 100% methanol −0.1% trifluoracetic acid over a period of 60 minutes, at a flow rate of 9.5 ml/min to give, after ion exchange on Amberlite IRA-400 (Cl⁻), the desired 2-(N-ethylcarboxamidino)-1,2,3,4,10,14b-hexahydrodibenzo[c,f] pyrazino[1,2-a]azepine hydrochloride m.p. 245°–250°.

The fractions were checked using an analytical column (3 mm×9 mm) under the same conditions. Deltapak is a trade mark of Millipore Pty. Ltd.

EXAMPLE 12 (FCC 18)

2-(N-Ethylthiocarboxamido)-1,2,3,4,10,14b-hexahydrodibenzo[c,f]pyrazino[1,2-a]azepine A solution of normianserin (5 g) in dry benzene (125 ml) was added slowly to a stirred solution of ethyl isothiocyanate (2 g) in dry benzene (125 ml). After 48 hours, the solvent was removed and the residue treated with hot diethyl ether (100 ml). The hot separated extract was cooled and poured into light petroleum (500 ml); on cooling, the desired product crystallised. It was collected and dried in vacuo, m.p. 97°–105°.

EXAMPLE 13 (FCC 16)

2-(Carboxamidomethyl)-1,2,3,4,10,14b-hexahydrodibenzo [c,f]pyrazino[1,2-a]azepine hydrochloride A solution of 2-chloroacetamide (270 mg) in benzene (20 ml) was added slowly to a solution of normianserin (720 mg) in benzene (20 ml) and the resulting mixture stirred for 7 days at room temperature. The reaction mixture was diluted with ether (40 ml) and extracted three times with 2N-hydrochloric acid (20 ml each time). Finally the residual solution was extracted twice with water (20 ml each time). All the aqueous extracts were combined, whereupon a cream coloured solid crystallised out. This was filtered off, washed and dried in vacuo to give the desired 2-(carboxamidomethyl)-1,2,3,4,10,14b-hexahydrodibenzo[c,f]pyrazino[1,2-a]azepine hydrochloride which decomposed above 220°.

EXAMPLE 14 (FCC 19)

2-(2-Carboxamidoethyl)-1,2,3,4,10,14b-hexahydrodibenzo[c,f]pyrazino[1,2-a]azepine A solution of normianserin (500 mg) and acrylamide (155 mg) in ethanol (40 ml) was heated at reflux for 12 hours. On cooling a colourless solid separated which was collected and dried in vacuo to give 2-(2-carboxamidoethyl)-1,2,3,4,10,14b-hexahydrodibenzo[c,f] pyrazino[1,2-a] azepine, m.p. 207°–211°.

EXAMPLE 15 (FCC 23)

2-(N-hydroxycarboxamidino)-1,2,3,4,10,14b-hexahydrodibenzo[c,f]pyrazino[1,2-a]azepine A mixture of cyanonormianserin (270 mg), hydroxylamine hydrochloride (140 mg) and sodium carbonate (424 mg) in N,N-dimethylformamide (5 ml) was stirred overnight at room temperature. The mixture was poured into water (100 ml) containing a small amount of ammonium chloride (500 mg) to give a gel-like precipitate. The gel was filtered at the pump, dried in vacuo, and the resulting amorphous mass crushed to give the desired product, m.p. 195°–200° with decomposition.

EXAMPLE 16 (FCC 5 alternate synthesis)

2-Carboxamidino-1,2,3,4,10,14b-hexahydrodibenzo [c,f]pyrazino[1,2-a]azepine Hydrochloride A mixture of the hydrochloride salt of normianserin (200 mg) and cyanamide (32 mg) in propan-1-ol (10 ml) was refluxed under an atmosphere of nitrogen for 24 hours. The solvent was removed and the resultant gum dispersed in aqueous ammonium chloride solution (10% w/v, 100 ml) then worked up in the usual fashion to give a product identical to that obtained according to the method of Example 2, as shown by melting point and mass spectrum.

EXAMPLE 17 (FCC 22)

2-(2-imidazolyl)-1,2,3,4,10,14b-hexahydrodibenzo[c,f]pyrazino[1,2-a]azepine

A solution of 2-(2-Imidazolino)-1,2,3,4,10,14b-hexahydrodibenzo[c,f]pyrazino[1,2-a]azepine p-toluenesulphonate prepared as in Example 3 (100 mg) and 2,3-dichloro-5,6-dicyanobenzoquinone (DDQ: 51 mg) in dry benzene (5 ml) was stirred overnight at room temperature, after which time a solid separated. The mixture was diluted with dichloromethane (50 ml) and washed three times with 5% sodium hydroxide solution (50 ml each time) the organic solvent dried, and evaporated to give a green solid which was triturated with hot propan-2-ol (approx. 100 ml), dried and crushed to give 2-(2-imidazolyl)-1,2,3,4,10,14b-hexahydrodibenzo[c,f]pyrazino[1,2-a]azepine as a pale green solid, m.p. above 250° (decomp.)

EXAMPLE 18

2-Carboxamidino-1,3,4,14b-tetrahydro-2H-pyrazino (1,2-d)dibenzo(b,f)(1,4)-oxazepine Hydrochloride A solution of oxamianserin (2.6 g) in anhydrous benzene (10 ml) is added slowly to a stirred solution of cyanogen bromide (1.2 g) in anhydrous benzene (10 ml) under an atmosphere of nitrogen. The mixture is stirred for 24 hours, then diluted with diethyl ether (30 ml) and shaken with water (25 ml). The separated aqueous layer is back extracted with a mixture of benzene and ether (equal volumes of each, total 50 ml) and the combined organic layers dried over anhydrous potassium carbonate to give a white solid, i.r. $v_{max}$ 2200 which is shown to be 2-cyanonoroxamianserin. The compound is not purified but is reacted with a solution of sodamide in liquid ammonia which is prepared in the usual way from metallic sodium (0.18 g in dried liquid ammonia (100 ml) in the presence of a trace of ferric nitrate). The reaction mixture is kept at about −70° and moisture rigorously excluded. 2-Cyanonoroxamianserin (1.7 g) is then added slowly and the mixture stirred whilst dried hexamethylphosphoric triamide (HMPA) is added dropwise until the 2-cyanonoroxamianserin begins to dissolve; about 1 ml of HMPA is required. A deep orange solution is formed. The stirring is continued for 30 minutes and the solution poured cautiously into a solution of ammonium chloride (2 g) in iced water (100 ml). The product is isolated in the usual fashion and recrystallised from isopropanol to give 2-carboxamidino-1,3,4,14b-tetrahydro-2H-pyrazino(1,2-d)-dibenzo(b,f) (1,4)-oxazepine hydrochloride as a colourless solid; it melts at 300°–310° C. with decomposition. The product has variable water content, depending on the drying procedure used.

EXAMPLES 19 to 28

The following compounds of the formula I are prepared by methods similar to those described in Examples 1 to 5:

| Example No. | X = | $R^3$ = | $R^1$ | Z = |
|---|---|---|---|---|
| 18 | O | H | H | NH |
| 19 | O | H | H | O |

-continued

| Example No. | X = | R³ = | R¹ | Z = |
|---|---|---|---|---|
| 20 | O | H | 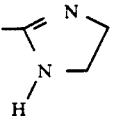 | |
| 21 | O | H | 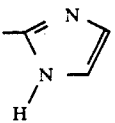 | |
| 22 | O | H | H | S |
| 23 | CH₂ | H | PhOCH₂CHCH₃ | NH |
| 24 | CH₂ | H | H | NOH |
| 25 | CH₂ | H | CH₃CH₂ | N.NH₂ |
| 26 | N.CH₃ | H | H | NH |
| 27 | S | H | H | NH |

Ph = phenyl

EXAMPLE 29

Pharmacological Activity of Compounds of the Invention

The compound of Example 2 was found in low concentrations to inhibit contractions of the guinea-pig isolated ileum and rat isolated stomach strip caused by histamine and 5-hydroxytryptamine respectively. The antagonism to both amines was persistent and non-competitive in nature, being relatively resistant to washing. After intravenous injection into rats and cats at doses of 0.1 mg/kg body weight or greater, it was found to cause long-lasting rises in arterial blood pressure and heart rate, accompanied by potentiation of the pressor responses to noradrenaline and sympathetic nerve stimulation with blockade of the pressor responses of the indirectly acting sympathomimetic agent tyramine. Concomitantly, the depressor effects of histamine were blocked, as were the pressor effects of 5-hydroxytryptamine for over 30 minutes. The pressor effects of 5-hydroxytryptamine in anaesthetised and pithed rats were inhibited by intravenous doses of 0.3-1.0 mg/kg body weight. Slightly higher doses reduced the bradycardia and the depressor response (the Bezold-Jarisch reflex mediated by 5-HT₃ receptors) to 5-hydroxytryptamine in anaesthetised rats. The drug inhibited oedema in the rat paw caused by intraplantar 5-hydroxytryptamine. The ratio of the oral to subcutaneous dose causing this effect indicated relatively good oral absorption. In mice it inhibited diarrhoea caused by L-5-hydroxytryptophan. In guinea pigs, intravenous doses of 0.03 mg/kg and above reduced the bronchoconstrictor effects of histamine and 5-hydroxytryptamine.

In four test situations, using the rat (spinal flexor reflex and morphine induced catalepsy), the mouse (L-5-hydroxytryptophan-induced head twitch) and behavioural changes in the cat, the compound of Example 2 failed to demonstrate any inhibitory or other actions on the central nervous system, whereas mianserin, in low doses, was effective in the former three tests. No overt behavioural changes or acute toxicity were seen in conscious cats after relatively large subcutaneous doses of the compound of Example 2. These data constitute very strong evidence that this compound does not penetrate into the central nervous system to cause central effects.

Intravenous doses of the compound of Example 3 of 0.1 mg/kg or above depressed the pressor responses to 5-hydroxytryptamine in the rat and also caused rises in arterial blood pressure. In cats, the effects of the ganglion stimulant McNeil -A-343 and histamine were reduced. Following intravenous injection into guinea-pigs, 0.01 mg/kg reduced histamine and 5-hydroxytryptamine induced broncho-constriction. Concentrations of 1 μg/ml or greater relaxed the isolated rat uterus in vitro.

The compound of Example 4 when injected into rats at intravenous doses of 0.3 mg/kg or greater reduced the pressor effects of 5-hydroxytryptamine and also the depressor effects of histamine. In cats, the effect of histamine was reduced after these doses also. In guinea pigs, intravenous doses of 0.01 mg/kg or greater reduced the bronchoconstriction caused by histamine or 5-hydroxytryptamine but had smaller effects on arterial blood pressure and heart rate than did the compound of Example 2, indicating some dissociation of sympathomimetic activity. In vitro at concentrations of 0.1 μg/ml or greater, this drug reduced the contractions of the isolated rat uterus caused by 5-hydroxytryptamine or high potassium concentrations and also demonstrated an anti-spasmodic action.

The compound of Example 5 was found to possess interesting actions on the central nervous system. Thus doses of 1 mg/kg given intraperitoneally attenuated the facilitation of spinal reflex activity caused by p-chloroamphetamine, and also the facilitation of spinal reflexes induced by fenfluramine in spinal and decerebrate rats. In contrast, the drug did not antagonise the facilitation of spinal reflexes caused by clonidine at these dose levels. The drug in doses of 10 and 20 mg/kg intraperitoneally and in doses of 20 mg/kg by mouth attenuated morphine-induced catalepsy. We conclude therefore that this drug is an orally active drug with central actions, particularly affecting serotonergic mechanisms, but has no effect in vitro (Table 1). This drug also showed peripheral actions. Thus it was found after intravenous doses of 0.03 mg/kg to reduce histamine and 5-hydroxytryptamine bronchoconstriction in the guinea pig.

EXAMPLE 30

Effects on Induced Contraction of the Isolated Guinea-Pig Ileum

Compounds according to formula I were tested for their ability to block contractions of the isolated guinea pig ileum induced by KCl, carbachol, or histamine at a concentration of $10^{-7}$M. Ileum preparations were prepared according to standard methodology. The results are summarized in Table 1. The concentrations shown are the minimum required to show activity.

TABLE 1

| Compound | | Effect on | | |
|---|---|---|---|---|
| Example | FCC no. | KCl | Carbachol | Histamine |
| 2 | 5 | ND | — | ++ $10^{-8}$ M |
| 4 | 9 | — | — | ++ $10^{-8} - 10^{-7}$ M |
| 3 | 11T | — | — | ++ $10^{-8}$ M |
| 9 | 12 | — | — | ++ $10^{-8} - 10^{-7}$ M |
| 5 | 13 | — | — | ++ $10^{-8} - 10^{-7}$ M |
| 7 | 14 | — | — | ++ |

TABLE 1-continued

| Compound | | Effect on | | |
|---|---|---|---|---|
| Example | FCC no. | KCl | Carbachol | Histamine |
| 10 | 15 | — | — | $\pm$ $10^{-8} - 10^{-7}$ M $10^{-7}$ M |
| 13 | 16 | — | — | $++$ $10^{-8} - 10^{-7}$ M |
| 11 | 17 | — | — | $++$ $10^{-8} - 10^{-7}$ M |
| 12 | 18 | — | — | $++$ $10^{-8} - 10^{-7}$ M |
| 14 | 19 | — | — | $++$ $10^{-8} - 10^{-7}$ M |

ND = not done; — no effect; + block; + + complete block

On the basis of preliminary results it appears that compounds FCC 16 and FCC 19 (Examples 13 and 14) are able to penetrate into the CNS, while compound FCC 12 (Example 9) is not.

Compound FCC 17 (Example 11) caused complete block of the effect on blood pressure, but not the effect on heart rate, in the chloral-anaesthetized rat, of both histamine and 5-hydroxytryptamine.

Thus the pharmacological properties of the novel compounds according to the invention are substantially different from those of mianserin. The compounds investigated possess the following properties:

1. Sympathomimetic activity
   increase in heart rate,
   increase in cardiac output,
   increase in arterial blood pressure,
   augmentation or depression of adrenergic nerve function
   potentiation or reduction of responses to sympathetic nerve stimulation in anaesthetised cats and rats
   potentiation of responses to noradrenaline and sympathetic nerve stimulation in anaesthetised cats and rats (some of the compounds lack this activity).

2. Anti-histamine and anti-5-hydroxytryptamine activity in cats, rats and guinea pigs The relative prominence of all these effects depends on the dose of the compound and on its structure. Effects were observed after intravenous doses of 0.01 mg/kg and above.

Some of these compounds would be expected to gain access to the central nervous system, whilst the more basic compounds will penetrate the blood-brain barrier less readily.

3. Antagonism of histamine and 5-hydroxytryptamine in isolated preparations, such as the guinea pig ileum and rat stomach fundus strip, with some drugs showing dissociation of the two types of activity Some (such as Example 2) are less likely than mianserin to cause side effects associated with actions in the central nervous system.

It is clear that the transmitter substance 5-hydroxytryptamine acts both in the central nervous system and periphery by actions at a number of distinct receptor sites. These have been termed 5-HT$_1$, 5-HT$_2$ and 5-HT$_3$. These three receptors have been further characterised into a number of sub-types (Fozard, TIPS, 1987, Volume 8, p.501). It has been noted that currently available evidence suggests that drugs affecting these receptors will be of use in the treatment of asthma, anxiety, depression, hypertension, migraine attacks, venous stasis, thrombosis, schizophrenia, diseases of the gastro-intestinal tract, emesis and as appetite stimulants. The inability of some of these compounds to pass into the central nervous system provides useful peripheral selectivity.

The compounds according to the invention are useful as anti-depressant, anti-hypertensive and anti-asthmatic agents. The ability of the compounds to increase cardiac output shows that they are valuable agents in the treatment of congestive heart failure. The anti-histamine and anti-5-hydroxytryptamine activity shows that the compounds are useful for treatment of allergic conditions and of diarrhoea and migraine.

The new compounds may be applied as drugs, for example, in the form of pharmaceutical preparations. For that purpose they are mixed with one or more pharmaceutical vehicles suitable for oral administration, or with liquid or solid auxiliaries, such as water, benzylalcohol propylene glycol, polyalkylene glycols, vegetable oils, gelatin, starch, lactose and magnesium stearate. The preparations may be shaped into tablets, coated tablets, grains, pills or capsules, or they may occur in liquid form, such as solutions, emulsions or suspensions. In the latter form they are also suitable for intramuscular or subcutaneous injections. Furthermore they may be used in the form of suppositories. They may also contain the required auxiliaries, such as fillers, lubricants, preservatives and emulsifying agents and are prepared by any method known per se.

The daily dosage may vary from 0.5 to 800 mg of the active substance, dependent upon the way in which they are to be administered, as well as the nature and the degree of the biological activity.

The compounds may also be applied for external use by introducing them into a spray together with a suitable propellant and, if desired, a solvent, further as a fine powder together with a suitable filler, and as a cream in combination with known auxiliaries.

It will be clearly understood that the invention in its general aspects is not limited to the specific details referred to hereinabove.

We claim:

1. A compound of the general formula I

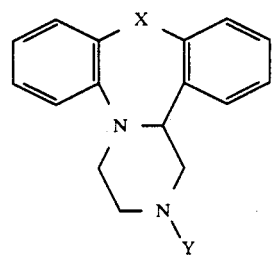

(I)

wherein
X = CH$_2$, O, S or NR$^4$, and

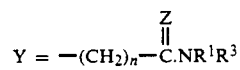

where R$^1$ = H, lower alkyl or an aryloxyalkyl group wherein the aryl group is optionally substituted by alkyl, alkoxy, halogen, alkyl substituted by halogen, and n is an integer between 0 and 5, and
Z = O, S or NR$^2$
wherein R$^2$ = H, lower alkyl, hydroxy, amino, cyano, or acyl,
R$^3$ = H or lower alkyl, and
R$^4$ = H, lower alkyl, or lower acyl, and pharmaceutically acceptable salts thereof.

2. A compound according to claim 1, in which X is CH₂ and Y is selected from the group consisting of

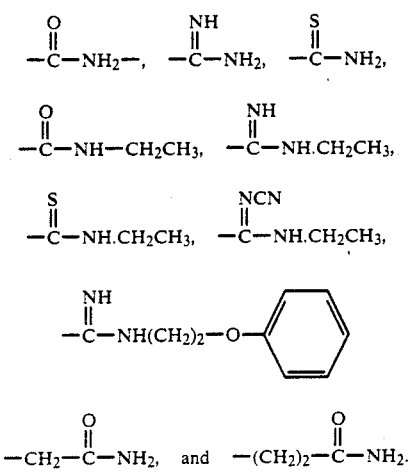

3. A compound according to claim 1 or claim 2, in which X is CH₂ and Y is $$-\overset{\overset{NH}{\|}}{C}-NH_2.$$

4. 2-Carboxamidino-1,2,3,4,10,14b-hexahydrodibenzo [c,f]pyrazino[1,2-a]azepine hydrochloride.

5. 2-(2-Imidazolino)-1,2,3,4,10,14b-hexahydrodibenzo [c,f]pyrazino[1,2-a]azepine p-toluenesulphonate.

6. 2-Thiocarboxamido-1,2,3,4,10,14b-hexahydrodibenzo [c,f]pyrazino[1,2-a]azepine.

7. 2-Carboxamido-1,2,3,4,10,14b-hexahydrodibenzo [c,f]pyrazino[1,2-a]azepine.

8. 2-(N-Cyano-N'-ethylcarboxamidino-1,2,3,4,10,14b-hexahydrodibenzo[c,f]pyrazino[1,2-a]azepine.

9. 2-(N-2-Phenoxyethylcarboxamidino)-1,2,3,4,10,14b-hexahydrodibenzo[c,f]pyrazino[1,2-a]azepine hydrochloride.

10. 2-(N-Ethylcarboxamido)-1,2,3,4,10,14b-hexahydrodibenzo[c,f]pyrazino[1,2-a]azepine.

11. 2-(N-Ethylcarboxamidino)-1,2,3,4,10,14b-hexahydrodibenzo[c,f]pyrazino[1,2-a]azepine hydrochloride.

12. 2-(N-Ethylthiocarboxamido)-1,2,3,4,10,14b-hexahydrodibenzo[c,f]pyrazino[1,2-a]azepine.

13. 2-(Carboxamidomethyl)-1,2,3,4,10,14b-hexahydrodibenzo [c,f]pyrazino[1,2-a]azepine hydrochloride.

14. 2-(2-Carboxamidoethyl)-1,2,3,4,10,14b-hexahydrodibenzo[c.f]pyrazino[1,2-a]azepine.

15. 2-(N-hydroxycarboxamidino)-1,2,3,4,10,14b-hexahydrodibenzo[c,f]pyrazino[1,2-a]azepine.

16. A method of treatment of disturbances of 5-hydroxytryptamine metabolism in a mammal, comprising the step of administering to a mammal suffering from such disturbance a pharmacologically effective amount of a compound according to claim 1.

17. A method according to claim 16, for treatment of a condition selected from the group consisting of depression, hypertension, congestive heart failure, migraine, anxiety, schizophrenia, gastrointestinal disturbances, diarrhoea and emesis.

18. A method of treatment of disturbances of histamine metabolism in a mammal, comprising the step of administering to a mammal suffering from such disturbances a pharmacologically effective amount of a compound according to claim 1.

19. A method according to claim 18 for treatment of asthma or an allergic condition.

20. A composition comprising as effective ingredient a compound according to claim 1, together with a pharmaceutically acceptable diluent, carrier or excipient.

21. A composition according to claim 20 for oral, rectal, intra-nasal or intra-vaginal administration.

22. A method for producing a compound according to claim 1 comprising reacting normianserin with a compound of the formula R¹NHCN wherein R¹ is as defined.

23. A method for producing a compound according to claim 1 comprising reacting normianserin with a compound of formula 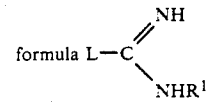

wherein R¹ is as defined and L is a leaving group selected from the group consisting of CH₃O, CH₃S, CH₃SO₂, SO₃H, and 3,5-dimethylpyrazol-1-yl.

24. A method for producing a compound according to claim 1 comprising reacting N-cyanonormianserin with H₂S to form a compound of formula I in which Z is S, then reacting said compound with R¹R³NH to form a compound of formula 1 where Z is NR².

25. A method for producing a compound according to claim 1 comprising reacting normianserin with ethyl isocyanate or ethyl isothiocyanate.

26. A method for producing a compound according to claim 1 comprising reacting cyanonormianserin with a p-toluene sulphonate to form a imidazolinyl compound, and optionally oxidizing the imidazolinyl compound.

27. A method for producing a compound according to claim 1 comprising reacting N-cyanonormianserin with H₂S to form a compound of formula 1 in which Z is S and then reacting the thus-formed product with methyl iodide in a second step, and reacting the product of the second step with R¹R³NH to form a compound of formula 1 where Z is NR².

28. A method for producing a compound according to claim 1 comprising reacting N-cyanonormianserin with methanol under acid conditions, and reacting the thus-formed product with R¹R³NH.

29. A method for producing a compound according to claim 1 comprising reacting N-cyanonormianserin with sodamide or with a metallated residue thereof.

30. A method for producing a compound according to claim 1 wherein X is CH₂, comprising the step of reacting normianserin under nucleophilic conditions with a compound selected from the group consisting of S,S-dimethyl N-cyanodithioiminocarbonate, 2-chloroacetamide, cyanamide, acrylamide, and 3-bromopropyl-1-cyanide.

* * * * *